(12) United States Patent
Roukes et al.

(10) Patent No.: US 7,330,795 B2
(45) Date of Patent: Feb. 12, 2008

(54) METHOD AND APPARATUS FOR PROVIDING SIGNAL ANALYSIS OF A BIONEMS RESONATOR OR TRANSDUCER

(75) Inventors: Michael L. Roukes, Pasadena, CA (US); Scott E. Fraser, La Canada, CA (US); Jerry E. Solomon, Glendale, CA (US)

(73) Assignee: California Institute of Technology, Pasadena, CA (US)

( * ) Notice: Subject to any disclaimer, the term of this patent is extended or adjusted under 35 U.S.C. 154(b) by 280 days.

(21) Appl. No.: 10/502,466

(22) PCT Filed: May 7, 2003

(86) PCT No.: PCT/US03/14286

§ 371 (c)(1),
(2), (4) Date: Jul. 7, 2005

(87) PCT Pub. No.: WO03/095617

PCT Pub. Date: Nov. 20, 2003

(65) Prior Publication Data

US 2006/0155478 A1   Jul. 13, 2006

Related U.S. Application Data

(60) Provisional application No. 60/379,507, filed on May 7, 2002, provisional application No. 60/379,618, filed on May 7, 2002, provisional application No. 60/379,555, filed on May 7, 2002, provisional application No. 60/379,712, filed on May 7, 2002.

(51) Int. Cl.
*G01N 33/50* (2006.01)

(52) U.S. Cl. .......................... 702/19; 702/22; 702/189
(58) Field of Classification Search ............ 702/21–25, 702/27–29, 30–33, 41–44, 56, 115, 189–191, 702/193–195; 73/61.75, 580; 700/266
See application file for complete search history.

(56) References Cited

U.S. PATENT DOCUMENTS

| 3,900,876 | A | * | 8/1975 | Tsukada et al. | 342/396 |
| 4,695,817 | A | * | 9/1987 | Kurtz et al. | 338/4 |
| 5,444,736 | A | * | 8/1995 | Kawashima et al. | 375/219 |
| 5,814,468 | A | * | 9/1998 | Siiman et al. | 435/7.21 |
| 2003/0043925 | A1 | * | 3/2003 | Stopler et al. | 375/254 |
| 2003/0137216 | A1 | * | 7/2003 | Tamayo de Miguel et al. | 310/311 |
| 2003/0138875 | A1 | * | 7/2003 | Powers et al. | 435/34 |

* cited by examiner

*Primary Examiner*—Manuel L. Barbee
(74) *Attorney, Agent, or Firm*—Foley & Lardner LLP

(57) ABSTRACT

An outputs signal, v(t), is generated from a bioNEMs transducer and mixed with a reference signal and then filtered to generate a correlator output, r(t). The correlator output is detected to generate a signal u(t) and then determined whether the signal u(t) satisfies a predetermined threshold. If qualified, it is then decided whether the signal u(t) represents a predetermined type of interaction between a free ligand in a fluid in which the NEMS device is immersed and a receptor attached to the transducer. The threshold is the Neyman-Pearson criterion based on a predetermined probability of false detection, Pfa. The interaction may be binding of a free ligand to the receptor or releasing a bound ligand from the receptor by competitive binding with the free ligand. The step of detecting comprises detecting the envelope of the signal, r(t).

40 Claims, 6 Drawing Sheets

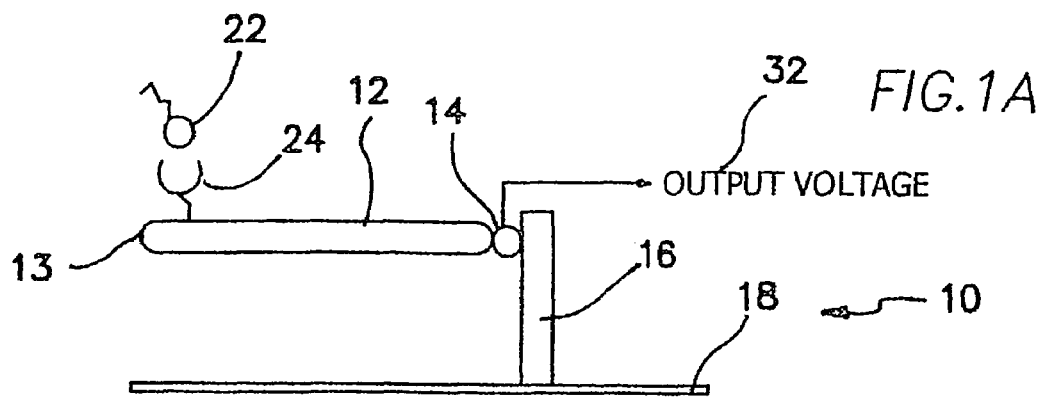
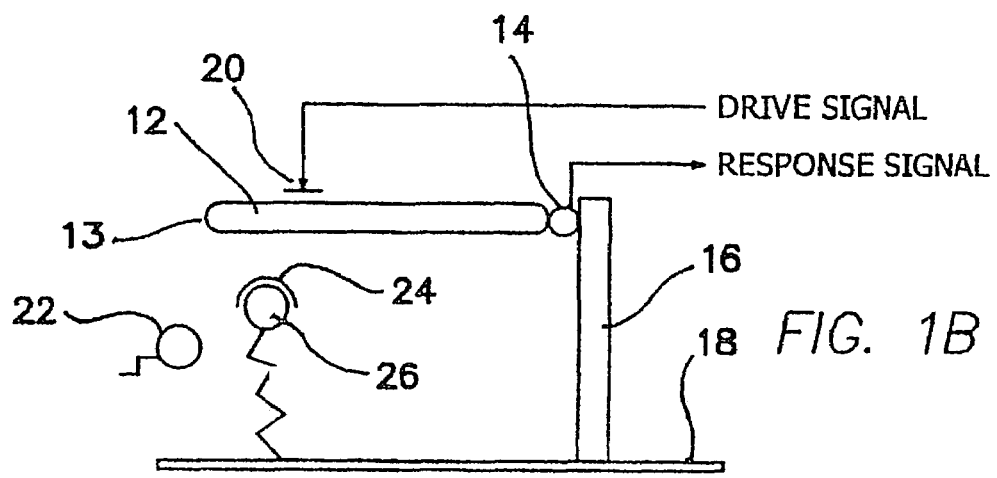
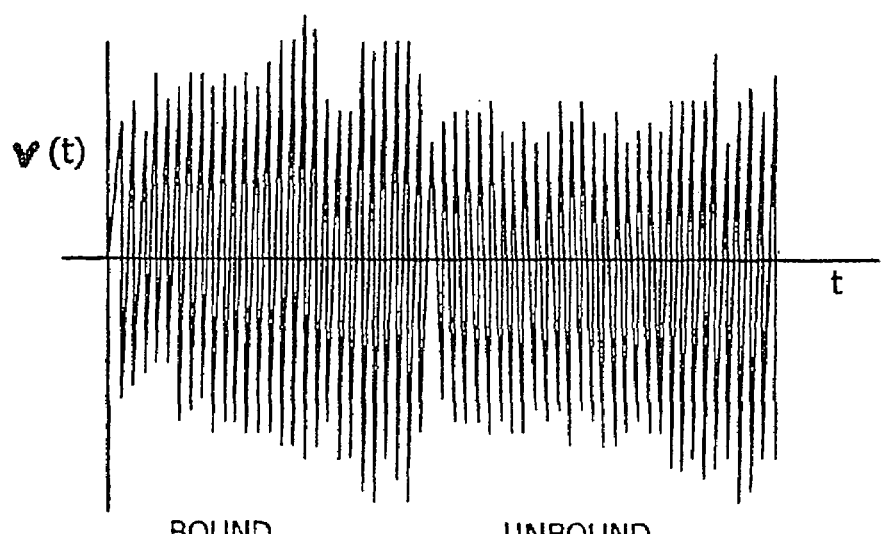

METHOD AND APPARATUS FOR PROVIDING SIGNAL ANALYSIS OF A BIONEMS RESONATOR OR TRANSDUCER

RELATED APPLICATIONS

The present application is related to U.S. Provisional Patent Applications Ser. No. 60/379,507, filed on May 7, 2002; Ser. No. 60/379,712, filed on May 7, 2002; Ser. No. 60/379,618, filed on May 7, 2002; and Ser. No. 60/379,555, filed on May 7, 2002, which are incorporated herein by reference and to which priority is claimed pursuant to 35 USC 119.

INCORPORATION OF COPENDING APPLICATIONS

It is to be expressly understood that the present application incorporates by reference simultaneously filed applications serial no. (PAU.34), entitled, "An Apparatus And Method For Vacuum-Based Nanomechanical Energy, Force, And Mass Sensors"; and serial no. (PAU.36), entitled "Dynamics Bionems Sensors And Arrays Of BIONEMS Sensor Immersed In Fluids" as if set out in their entirety. Further, the present application incorporates by reference U.S. patent application Ser. No. 10/138,538, filed on May 3, 2002 entitled, "An Apparatus and Method for Ultrasensitive Nanoelectrochemical Mass Detection"; and U.S. patent application Ser. No. 09/927,779, filed on Aug. 9, 2001, entitled, "Active NEMS Arrays for Biochemical Analyses" as if set out in their entirety.

FEDERAL SUPPORT STATEMENT

The U.S. Government has certain rights in this invention pursuant to Grant No. ZF49620-02-1-0085 awarded by the United States Air Force Office of Scientific Research (AFOSR).

BACKGROUND OF THE INVENTION

1. Field of the Invention

The invention relates to nanoelectromechanical devices and methods as applied to biological or medical 2. Description of the Prior Art There have been a number of recent advances in NEMS and in Chemical Force Microscopy (CFM). NEMS approaches have resulted in a family of cantilevers of small length and thickness that can resonate at high frequency with high Q. When operated in ideal conditions (low T, vacuum) these NEMS devices show unprecedented sensitivity. "NEMS" in this specification is used to mean devices with at least one dimension which is equal to or smaller than one micron. It does not exclude the possibility that the "NEMS" device may have one or more other dimensions larger than one micron. Furthermore, as can be understood there is often no sharp line of distinction between the characterization of a device at or below one micron in size and one which is above one micron. The more meaningful significance to the term, "NEMS" is that the device in question shares some characteristic with similar devices scaled to submicron sizes or which is unique to submicron devices or operation.

On a much larger size scale (Atomic Force Microscopy (AFM), CFM) work in several groups has been directed at analyzing the forces exerted by interactions between single molecules, ranging from hydrogen bonds and antibody-antigen interactions to covalent bonds. AFM cantilevers, decorated with biomolecules and interacting with derivatized surfaces or with derivatized magnetic beads, demonstrate forces of order 100 pN for an antigen-antibody interaction and ~1-10 nN for a covalent bond. These watershed experiments show the feasibility of measuring chemical events at the stochastic limit, but also offered evidence of the difficulty of harvesting this potential in a small, portable and robust device.

According to the invention what is needed is some way of reducing the size of the cantilever to NEMS dimensions to offer the needed temporal response, small volume and sensitivity to single molecules needed to build a device with single cell capability. Of course, placing a NEMS cantilever in solution and at room temperature will call for a revision of detection strategy from those usually employed for either CFM or NEMS. The fluid will damp the NEMS cantilever making resonance detection impossible, and the thermal energy of the solution will buffet the cantilever.

What is needed is some way to exploit these to potential difficulties as an integral part of the assay.

In contrast to conventional CFM what is needed according to the invention is an approach which will not attempt to measure the force of a single (or small number of) chemical bond by recording cantilever deflection.

What is needed is some type of design for a NEMS cantilever will allow detection of the presence of a chemical bond by the restriction it produces in the otherwise large thermally driven motion of the cantilever using an integral sensor.

What is further needed according to the invention is a means of using an array of BioNEMS cantilevers with systematically different chemical decorations offers both high reliability and sensitivity to concentration.

Further, according to the invention what is needed is some way of interpreting the "noise" of fluctuations as signal, and biology the opportunity of assembling and employing a useful and robust assay.

Microarray technologies have provided significant recent advances in analyzing protein receptors and their ligands, as well as in analyzing gene expression profiles. For example, microarrays of a few thousand targets have become a major technique used by the drug discovery industry. These microarrays are created by photolithography, by microstamping, or by microdotting, resulting in an array of spots (20-100 $\square$m) on a substrate. The array is typically read by superfusing a fluorescently labeled analyte, over the array and determining the amount of binding by scanning the array with a micro-fluorimeter. Although these approaches are becoming increasingly widespread, the large size of the reader instrumentation and the intrinsic limitations of the fluorescence analysis employed make them completely inappropriate for applications in which both portability and robust performance are required. Furthermore, they are single-use devices, hence they cannot easily accommodate applications that require continuous monitoring. Finally, the devices rely on significant volumes of analyte, making them ill-suited to the most powerful recent advances in drug discovery provided by combinatorial chemistry or to the most sensitive assays of gene expression.

Another goal of the proposed studies is to develop a new technology of biochips at the nanoscale (BioNEMS) that is capable of sensing the binding of single biological molecules to their receptors. A growing literature of chemical force microscopy (CFM) has shown that a modified AFM can be tailored to measure the binding force of interactions ranging from single hydrogen bonds and single receptor-ligand interactions to single covalent bonds. The range of these forces are well within the capability of AFM instrumentation to detect; however, an AFM cantilever in solution does not have the temporal response characteristics needed to permit the binding and unbinding of biological ligands and their receptors to be followed reliably. Perhaps even more significant is the substantial size of the equipment required for performing AFM/CFM, and the well-known sensitivity of AFM to air-borne and surface vibrations.

What is needed is some type of technology that has the same success as CFM in detecting the forces of single molecular interactions, but is scaled down to NEMS scale to permit it to respond rapidly enough to follow the binding and unbinding events. Given the size of the chemical forces, the most robust mode for the BioNEMS to operate will be to forsake direct measurements of the force of binding. What is needed according to the invention is some type of means for using the ongoing fluctuations in the position of the NEMS cantilever followed using integral sensors to obviate the need for the support equipment used in AFM.

BRIEF SUMMARY OF THE INVENTION

According to the invention the motions of the NEMS cantilevers will be used to follow binding and unbinding events. The basic idea is that a cantilever that is not coupled at its tip by a receptor-ligand pair will fluctuate in its position more dramatically than a cantilever that is restricted by a ligand-receptor pair. Strong ligand-receptor bonds can partially arrest the cantilever motion for considerable time ($\sim t_{on}$ for the ligand-receptor pair); even weak interactions will alter the statistics of cantilever motion.

Moving down to the small size of NEMS devices offers several significant advantages. As already mentioned the small size of the NEMS devices permit them to be dramatically more responsive to the kinetics of binding and unbinding. This high frequency response is critical to following the stochastic nature of receptor ligand interaction, most receptor-ligand pairs interact dynamically, binding, remaining engaged for times ranging from microseconds to seconds (depending on the exact receptor-ligand pair), and then releasing. High frequency response (~MHz) is critical if an assay is to follow biomolecular interactions. The ability to resolve the opening and closing of individual membrane channels in the patch-clamp (gigaohm seal) technology has revolutionized our understanding of the physical biochemistry underlying neuronal function; before the patch-clamp, experimenters could only attempt to decode molecular mechanism from recordings of huge populations of membrane channels. It is our belief that the analysis of biomolecules is presently in exactly the same state, limited by both the vast quantities of materials required and the smearing in time inherent in even the most sensitive assays. BioNEMS are thus poised by the invention to truly move our analysis of biomolecules to the stochastic limit.

One of the powers of this approach is that it exploits the thermal motion of the cantilever, normally a major limitation in AFM, as a driving force. Furthermore, the noise of cantilever motion becomes smaller as cantilever size is decreased. In addition, the small size of NEMS devices permits an array of detectors ($\geq 500$ cantilevers) to be constructed in a small active volume ($\leq 1100$ pL). This latter advantage is of great significance, as it offers the promise of a technology for sensing the levels of RNA, proteins and second messengers present in single cells.

The BioNEMS approach of the invention offers a major reduction in the size and nature of the instrumentation needed for it to operate (in comparison to AFM/CFM). The sensor for the motion of the cantilever will be integral to the NEMS cantilever, which eliminates the size and density limits that would be imposed by the optical detection of cantilever motion used in AFM. This will permit the BioNEMS cantilevers to be much smaller and to be dramatically more closely packed than is practical in AFM.

As outlined in the section describing NEMS sensing below, integration of a piezoresistive transducer will offer sensitivity far greater than needed to record the NEMS cantilever motions in liquid water. As a result, with proper integration, the sensor, the detectors needed to follow cantilever motion, the logic needed to interpret the motions, and the circuitry needed to communicate the results can be packaged into a single device. In contrast to the promise of their names, current "DNA Chip" or "Proteomics Chip" technologies require bulky and heavy readers to interpret the binding of chemical species to a sensor package several centimeters in length and width. The BioNEMS approach outlined here offers the promise of package sizes consistent with the term "chip" (~DIP dimensions) and thereby offers a variety of applications that would be impossible or impractical by other approaches.

The goal of the proposed work is to exploit the thermally driven motion of the cantilever, and its modulation by receptor-ligand interactions. Knowledge of the physics of NEMS cantilevers in solution and of stochastic biochemistry will be used to interpret the motion of the cantilever. Thus, the construction of a working BioNEMS of this class requires a close collaboration between researchers working on NEMS fabrication, biologists working on the biochemical modification of device surfaces, physicists interested in the fluid dynamics of NEMS devices, and information scientists accomplished at extracting and analyzing data from arrays.

The BioNEMS research effort outlined here will have several thrusts, ranging from fundamental to applied science, and the development on new nanoscale fluidic technology. Our goal is to develop, understand and, thereby, to refine the techniques for the construction of BioNEMS and then demonstrate their novel uses.

Examples include:
Basic studies of the performance of NEMS in solution
Basic studies of single molecule chemistry
Cellular studies of hormones, growth factors and second messenger. The release of growth factors from cells is typically in too low of a concentration and too small a volume for direct analysis by traditional techniques.
Use of the BioNEMS as sensors for the output of combinatorial chemistry syntheses as a test in drug discovery efforts.
Use as a sensitive "gene chip" for the detection of DNA sequences, or as a sensor for biological hazards.
Use as a monitor of the concentration of environmental toxins.

The invention is defined as a method of sensing a signal from an oscillating bioNEMs resonator or transducer comprising the steps of generating an output signal, v(t), from the oscillation of the transducer. The term, "resonator" is used here to mean an oscillating NEMS device or structure, such as a flexural or torsional cantilever beam, a flexural or torsional doubly clamped beam or any combination of structures. The "resonator" or "transducer" need not be oscillating at resonance and its oscillation may be periodic, aperiodic or complexly harmonic. Its oscillation may be induced by any means known including ambient thermal vibrations or external applied electromagnetic, hydraulic or mechanical forces. The method continues with the step of mixing the output signal with a reference signal. The mixed output signal is filtered to generate a correlator output, r(t). The correlator output is detected to generate a signal u(t). It is then determined whether the signal u(t) satisfies a predetermined threshold. If qualified, it is then decided whether the signal u(t) represents a predetermined type of interaction between a free ligand in a fluid in which the NEMS device is immersed and a receptor attached to the transducer.

In the preferred embodiment, the step of determining whether the signal u(t) satisfies a predetermined threshold comprises the step of applying the Neyman-Pearson criterion based on a predetermined probability of false detection, $P_{fa}$. In another embodiment the step of determining whether the signal u(t) satisfies a predetermined threshold comprises the step of determining whether a likelihood ratio of probability density functions of bound and unbound configurations of the ligand and receptor has a predetermined value.

The step of deciding whether the signal u(t) represents an predetermined type of interaction between a free ligand in a fluid and a receptor attached to the transducer comprises in one embodiment the step of deciding based on u(t) whether the ligand has bound to the receptor. In another embodiment the step of deciding whether the signal u(t) represents an predetermined type of interaction between a free ligand in a fluid and a receptor attached to the transducer comprises the step of deciding based on u(t) whether a bound ligand has been released from the receptor by competitive binding with the free ligand.

The step of detecting the correlator output to generate a signal u(t) comprises squaring the signal, r(t) or in another embodiment comprises the step of detecting the envelope of the signal, r(t).

The method may further comprise the steps of sampling a plurality of measurements of the signal, u(t) and summing the sample signals to generate a signal, q(t), which is then tested for qualification relative to a threshold and from which qualified signals a decision is made as to the interaction which as occurred between the free ligand and receptor.

In yet another embodiment the invention is defined as a method of sensing a signal from an oscillating bioNEMs transducer comprising the steps of generating an output signal from the oscillation of the transducer; chopping the output signal in time; filtering the mixed output signal to generate a correlator output, r(t); generating summed and differenced quadrature components of the filtered chopped signal; multiplying the summed and differenced quadrature components together to generate a signal, z(t); integrating z(t) over a sample period, T, to generate a signal, u(t); summing multiple measurements of z(t) over N sample periods to generate a signal, q(t); determining whether the signal u(t) satisfies a predetermined threshold; and deciding whether the signal u(t) represents an predetermined type of interaction between a free ligand in a fluid and a receptor attached to the transducer.

The method further comprises the steps of providing the NEMS transducer with an attached bioreceptor; exposing the biofunctionalized transducer to a free ligand in fluid; interacting the free ligand with the bioreceptor to provide an interaction therebetween; and oscillating the transducer to detect the existence of the interaction between the bioreceptor and free ligand.

The step of generating a output signal from the oscillation of the transducer comprises oscillating a piezoresistive transducer by means of thermal fluctuations and/or by means of an external driving signal.

In one embodiment the step of generating a output signal from the oscillation of the transducer comprises the step of oscillating a piezoresistive transducer by means of oscillating a coupled second transducer by fluid coupling therebetween and/or by ligand coupling therebetween. The method may further comprise the step of providing a substrate and ligand coupling the transducer to the substrate.

In addition, the invention is defined as a bioNEMS apparatus for performing each of the foregoing methodologies.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1a is a diagram which shows a passive one-port device.

FIG. 1b is a diagram of the device of FIG. 1a used in an active mode.

FIG. 2a is a diagrammatic top view of the two beams. FIG. 2b is a diagrammatic side view of/the two beams between two substrates in a passive configuration. FIG. 2c a diagrammatic top view of the two beams in an active configuration.

FIG. 3 is a graph which shows a typical output expected from a device under the conditions of no target biomolecule being bound to the cantilever, and with a target molecule being bound.

Figure 2A:
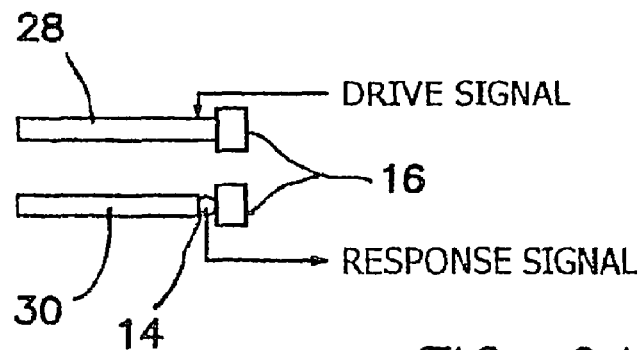
FIGS. 2a-2c show two possible active two-port device embodiments, where one cantilever beam is actively driven by a sinusoidal signal, and the other cantilever beam is a passive responder.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Physical Parameters that Govern SNR in Stochastic Signal Detection in BioNEMS Devices The illustrated embodiments disclose several signal detection strategies for several NEMS device configurations. Four embodiments are illustrated, the second of which is a simple variation of the first, which are shown in FIGS. 1a, 1b, 2a, and 2b. FIG. 1a shows a passive one-port device 10, while FIG. 1b shows the same embodiment using in an active mode, i.e. in which an external drive signal is applied to vibrate the cantilever. A submicron or NEMS cantilever beam 12 in FIG. 1a is coupled via a NEMS output device 14 to a support 16 mounted in turn on a substrate 18. Free ligand molecules 22 are available for binding to bound receptor molecules 24 on beam 12. In FIG. 1b a gate drive 20 is coupled to beam 12 and there is also bound ligands 26 on substrate 18 combined or combinable with receptors 24 on beam 12. Bound ligands 26 are identical to free ligands 22 except for being complexed with receptors 24.

Figure 2B:
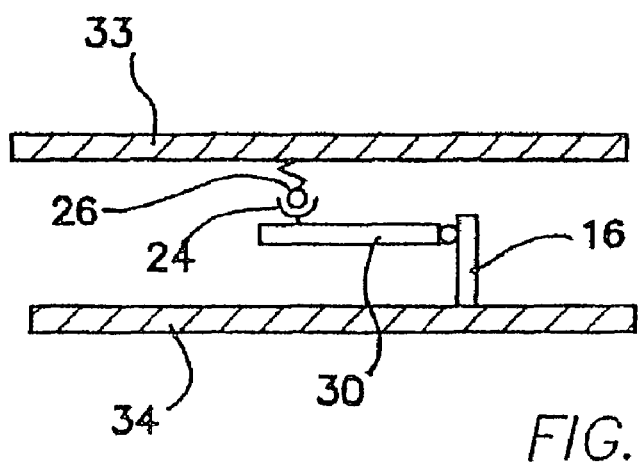

FIGS. 2a and 2b show two possible active two-port device embodiments, where one cantilever beam 28 is actively driven by a sinusoidal signal, and the other cantilever beam 30 is a passive responder, which is sympathetically driven by the motion of cantilever 28 by means of fluid coupling and/or other means. The sensed bioNEMS signal is generated by a change in the mechanical coupling between the two cantilevers 28 and 30. For the purposes of this analysis we assume the cantilever beam dimensions to be 10 nm×300 nm×3 μm (h,w,l), which yields a vacuum resonant frequency of 1.4 MHz, and a force constant, K, of 0.43 mN/m. It is to be expressly understood that the dimensions chosen are only illustrative and the invention applies to all sizes and types of NEMS cantilevers, beams or transducers and not just to the illustrated example.

Since we need to impose some specific requirements on the signal detection system, we have chosen to examine to specific NEMS device applications: (1) as a biomolecule assay device, e.g., detection of the presence of pathogens; and (2) as a device to study stochastic biochemistry. These two device applications impose a different set of requirements on the development of an optimal signal detection strategy. The most stringent of these is the time allowed for observation. In the second case of stochastic biochemistry, we are severely constrained by a short-time requirement, while in the first case of the detection of the presence of pathogens, we may take a more leisurely approach to accumulating data for integration. In addition the so-called bioinformatics requirements for these two devices are quite different, as will be made clear below.

We will consider first a detailed description of the device thermal noise characteristics that were used as the basis for signal detection analysis. Then we will provide a detailed description of the signal detection analysis methods used here. Finally we will provide a summary of the results, including detector performance curves for each of the cases illustrated. It is here that we provide detector performances directly in terms of the device parameters.

The simplest physical configuration of a BioNEMS device for the detection of the presence or absence of a particular target biomolecule comprises a single passive or undriven submicron cantilever 12 as shown in FIG. 1 is side diagrammatic view with a small area near the tip 13 containing some number of attached receptor molecules 24 specific for a target ligand of interest. In some cases this may be augmented by an adjacent cantilever structure 30 as shown in the diagrammatic side view of FIG. 2 and top view of FIG. 3 that is "clean", i.e., has no receptors attached, and is used a reference stochastic signal in a detection scheme as described below. The induction of motion or vibration in device 10 may be accomplished by any means now known or later devised, and may include such means as externally applied magnetomotive or electrostatic drive signals or ambient thermal fluctuations. The means by which cantilever 12 or 30 is excited or vibrated is not critical to the invention and many different excitation modes may be substituted.

Transverse vibrational motion of the cantilever 12 or 30 is sensed through use of a piezoresistive sensor 14 formed by a doping process in a small region where the cantilever 12 or 30 connects to its substrate 18 through a support 16. Thus, when the piezoresistor 14 is biased with a small current, transverse deflections of cantilever 12 or 30 cause a change in the resistance and hence the bias voltage; and these changes constitute the output signal of the BioNEMS device.

Given this configuration and means of producing an output signal proportional to transverse cantilever deflections, we need to relate the electrical output signal to changes in the physical characteristic of BioNEMS device 10 that are the result of target ligand binding to the cantilever-attached receptors 24. It should be kept in mind that device 10 will typically be immersed in a fluid environment in most bioNEMS applications as opposed to a vacuum in which NEMS devices are normally used, although air or other gases can be contemplated a possible fluid environments. Over the range of cantilever vibrational frequencies of approximately 10 to 600 kHz, the cantilever beam 12 deflection power spectral density (PSD) is well-approximated by the following expression:

$$S_x(\omega) = \frac{4k_B T \gamma_e \omega_0^2}{\kappa^2(\omega_0^2 + \omega^2)} \quad 3.1$$

where x denotes the transverse deflection of the cantilever tip 13, $\gamma_e$ is the effective damping constant due to fluid coupling with the cantilever environment, κ is an effective "spring constant" associated with the cantilever, and $\omega_0$ is defined by $$\omega_0 = \frac{\kappa}{\gamma}, \quad 3.2$$

The autocorrelation function at zero lag gives us an expression for the mean-square deflection fluctuations; we thus have $$\langle x^2(t) \rangle = R_x(0) = \frac{4k_B T \gamma_e}{\kappa^2} \quad 3.4$$

Since we are using a piezoresistive readout transducer 14, the mean-square voltage fluctuations at the BioNEMS device output will be given by $$\langle v^2(t) \rangle = \frac{4k_B T \gamma_e}{\kappa^2} [GI_0]^2 \qquad 3.5$$

where G is the transducer conversion coefficient, and I0 is its bias current.

We next examine how the binding of target ligands 22 to the cantilever receptors 24 generates a "signal". First, note that the device output voltage is a sample function of a stochastic process described by Eqs (3.1) and (3.4), and that the power spectral density (PSD) is relatively flat over the frequency range of interest. We thus take the probability density function (PDF) describing the output voltage to be zero-mean Gaussian, with a variance of $\sigma^2_0$. Since the process is a zero-mean process, the variance $\sigma^2_0$ is equal to the mean-square, and Eqn. 3.5 is the appropriate expression for the variance of the output voltage, v. For purposes of detecting the presence of bound target ligand molecules 26, we thus look for a change in the variance $\sigma^2_0$ of the device output voltage v. A rather qualitative view of the situation for bound and unbound cases is shown in FIG. 3. This assumes that binding of the target ligand 22 will increase the variance $\sigma^2_0$ of the output voltage v. As a matter of notation we will take $\sigma^2_b$ and $\sigma^2_u$ to denote the output variance for the bound and unbound cases respectively.

Now, if the size scale of the target ligand 22 is of the same order as the width of the cantilever 12, 28 or 30 to which it is bound, then we may expect that the major effect of ligand binding will be to increase the effective damping coefficient, $\gamma_e$. In this case it is appropriate to define the signal-to-noise ratio (SNR), in terms of power, as follows $$SNR = \frac{\sigma_b^2}{\sigma_u^2} = \frac{\gamma_{e,b}}{\gamma_{e,u}} \qquad 3.6$$

We note that this expression may also be valid for the case where the ligand-receptor complex 26, 24 is a relatively long, low-compliance structure.

Finally, for cases where ligand binding does not significantly alter the $\gamma_e$, it is possible that such binding events can modify the effective force (spring) constant, $\kappa$. In this case our expression for the SNR becomes $$SNR = \left[\frac{\kappa_u}{\kappa_b}\right]^2 \qquad 3.7$$

In order to determine quantitatively whether ligand binding will increase or decrease the effective force constant $\kappa$, we need a more accurate and detailed expression for the PSD than stated thus far. However, one might argue qualitatively that ligand binding will tend to decrease the effective force constant of the cantilever beam 12. A detailed description of the performance of a detection system designed for detecting stochastic BioNEMS output signals is given below.

Consider first device noise characteristics. In this analysis we assume that the noise at the output 32 is dominated by the thermal noise of the cantilever 12 or 30 due to the microfluidic coupling to the surrounding liquid environment. Laboratory measurements generally confirm this assumption. We therefore take the probability density function (pdf) describing the voltage fluctuations at the output 32 to be Gaussian noise with zero-mean and variance given by the mean-square voltage fluctuations. For the device 10 considered here, these assumptions hold rather well for frequencies below about 600 kHz, and the so-called force-noise spectral density is approximately 15 pN/$\sqrt{Hz}$, over the range of 10 kHz to 600 kHz. The cantilever beam deflection spectral density, due to the fluid damping of the beam 12, can be well-approximated by $$S_x(\omega) = \frac{4k_B T \gamma_e \omega_0^2}{\kappa^2(\omega_0^2 + \omega^2)} \qquad (1.1)$$

Of course, $k_B$ and T are Boltzmann's constant and the system temperature respectively. The corresponding autocorrelation function is:

$$R_x(\tau) = \frac{4k_B T \gamma_e}{\kappa^2} e^{-w|\tau|} \qquad 1.3$$

and from this we see that the mean-square displacement is given by $$R_x(0) = \langle x^2(t) \rangle = \frac{4k_B T \gamma_e}{\kappa^2} \qquad 1.4$$

Since we are using a piezoresistive readout transducer, the mean-square voltage fluctuations at the output of the device will be given by $$\langle v^2(t) \rangle = \langle x^2(t) \rangle [GI]^2 \qquad 1.5$$

where G is the transducer conversion coefficient, and I is its bias current. Finally, we note that the physical quantity that is affected by the binding of a large biomolecule to a cantilever 12 is $\gamma_e$, due to the additional viscous drag introduced by the molecule.

Consider now the signal detection analysis. Signal detection strategies for the four device configurations are described in turn, and expressions for the expected detection performance characteristics for each are derived. Since the object of the illustrated embodiment is to detect the absence or presence of a specific biomolecule attached to cantilever 12, 28 or 30, the term, "signal", is used to mean changes in the thermal noise characteristics at the output 32 due to the attachment of such molecules to cantilever 12, 28 or 30 in FIGS. 1a, 2a, 2b and 2c. The specific characteristic that we will use is the variance of the voltage at the output 32. Though this view changes slightly when we come to actively driven devices in FIG. 1b.

Thus, in general, the (power) signal-to-noise ratio (SNR), in dB, will be given by SNR=20 $\log_{10}(\sigma_b/\sigma_u)$, where $\sigma^2$ is the variance and the subscripts u and b denote the unbound and bound cases respectively. Note that for our zero-mean Gaussian assumption, the variance is simply equal to the mean-square.

One-Port Passive Configuration

FIG. 3 is a graph which shows a typical output expected from device 10 subject only to thermal fluctuations under the conditions of no target biomolecule being bound to the cantilever 12, and with a target molecule being bound.

Ignoring the fact that this output is actually thermal noise, it looks very much like a typical binary (on/off) signaling system, and in fact that is how we will treat it for purposes of a signal detection analysis. Since this is a zero-mean process, the variance is equal to the mean-square, i.e., $\sigma^2 = \langle v^2(t) \rangle$, where v(t) is the device output voltage. Thus, the SNR at the output of our device can be written as $$SNR_0 = 10\log_{10}\left(\frac{\langle v_b(t)\rangle^2}{\langle v_u(t)\rangle^2}\right) \quad 1.6$$

where we have cast it in terms of the voltages at the output 32. Note that according to Eq 1.4 above, the variance of the device output voltage will be proportional to $\gamma_e$, and for our passive configuration the capture of a biomolecule by the cantilever 12, 28 or 30 will result in an increase in $\gamma_e$.

In general, the way in which we attempt to increase the overall SNR is by reducing the amount of noise relative to the amount of signal. This is usually done by using a narrowband system, where the device noise is wideband, and the signal is narrowband. Thus, the overall SNR can be improved by limiting the system bandwidth to only that sufficient for containing all of the signal energy. Now, if we consider the case of the passive configuration from this viewpoint, we can easily see that there is effectively no way to improve the SNR for this configuration beyond $SNR_0$, since "narrowbanding" affects the signal and noise in exactly the same way.

With the above argument in mind, we proceed to analyze the expected performance of this configuration based on standard hypothesis testing methods, using the Neyman-Pearson criterion for setting our detection threshold. In order to convert the device output voltage from an alternating voltage to a "D.C." voltage, we will assume the use of an absolute value conversion operation. Note that our final results for this configuration do not depend upon this choice. Since we have assumed a Gaussian probability density function for the noise at the output 32, the probability density function for the output of the absolute value converter will be given by $$f_x(x_i) = \frac{2}{\sigma_i\sqrt{2\pi}} e^{-\frac{x_i^2}{2\sigma_i^2}}, x > 0 \quad 1.7$$

where i=u, b refers to the variance in the cases of unbound and bound respectively, and $x_i(t)=|v_i(t)|$. For the passive configuration we have $H_0: x(t)=x_u(t)$ $H_1: x(t)=x_b(t)$ for the hypotheses to be tested. One traditional method of determining the detection threshold is to use the likelihood ratio $$\lambda(x)=f_x(x_b)/f_x(x_u) \quad 1.8$$

The decision criterion is simply: If $f_x(x_b)$ is greater than $f_x(x_u)$ then choose $H_0$, otherwise choose $H_1$. Note that, due to the nature of our detection system, this is the inverse of what is usually encountered in signal detection practice. The use of this threshold yields a maximum likelihood detection system.

However, this approach does not allow the flexibility that we need for our problem, so we will use instead the Neyman-Pearson method to determine the threshold. For a given probability of false alarm ($P_{fa}$), and SNR, this method yields the maximum probability of detection ($P_d$). The Neyman-Pearson criterion is quite simple, and consists of determining the threshold, $\lambda_0$, from the $P_{fa}$ as follows $$P_{fa} = \int_{\lambda_0}^{\infty} f_x(x_u) dx = \eta \quad 1.9$$

where $\eta$ is the required $P_{fa}$. Note that all the performance curves shown below are parameterized in terms of $\eta$. The other quantity that we need is the probability of detection, ($P_d$), which is given by $$P_d = 1 - \int_{-\infty}^{\lambda_0} f_x(x_b) dx \quad 1.10$$

Putting these expressions in terms of the applicable probability density functions, we have $$P_{fa} = \frac{2}{\sigma_u\sqrt{2\pi}} \int_{\lambda_0}^{\infty} e^{-x_u^2/2\sigma_u^2} dx = \eta \quad 1.11$$

$$P_d = 1 - \frac{2}{\sigma_b\sqrt{2\pi}} \int_{-\infty}^{\lambda_0} e^{-x_b^2/2\sigma_b^2} dx \quad 1.12$$

Of course our system will not be directly measuring the quantities used above, but will actually employ an envelope detector described in connection with FIGS. 4 and 5. Therefore we compute performance characteristics for this case assuming the NEMS output 32 is passed through a narrowband filter 36, followed by the envelope detector 38. Note, recalling the above discussion about the effects of bandwidth limiting, we are not attempting to increase SNR by using a narrowband filter 36. It is simply used here for analysis convenience. Now, the envelope of a narrowband Gaussian process has a probability density function given by $$f_q(q) = \frac{q}{\sigma_i^2} e^{-q^2/2\sigma_i^2} \quad 1.13$$

where q=|r|, with r(t) being the output of the narrowband filter 36; and i=u, b for the unbound and bound cases respectively. This probability density function is called a Rayleigh density, and this is the density function that we will use to compute the $P_{fa}$ and $P_d$ for this configuration.

Active Configurations

Active configurations are comprised of one or two cantilevers 28, 30, one of which 28 is actively driven by a sinusoidal deflection voltage, and the response to this by cantilever 30 constitutes the signal. From a signal detection standpoint, all of the active configurations considered here can be treated in the same way. At the end of this analysis we will point out where there might be some modest differences among the configurations. When treating a narrowband signal-plus-noise problem, it is usual to consider either an envelope detector (absolute value detector), or a square-law (quadratic) detector, either of which is denoted by reference numeral 38. Now, a variety of studies have shown that, in the small SNR regime, the behavior of these two detectors are essentially equivalent, so we shall mostly assume a square-law detector 38 for purposes of analysis. In practice we prefer to use an envelope detector 38, which is easier to implement and has slightly better performance at small SNR.

Assuming a square-law detector 38, we will analyze two processing procedures: (1) single-observation processing, and (2) multiple observation processing, i.e., post-detection summation. In general, we assume the signal to be either one of the two forms:

$$r(t)=n(t),$$

$$r(t)=A\cos(w_0 t+\theta)+\eta(t),$$

for the noise only, and "signal" plus noise cases with n(t) being the noise function. Again we assume that n(t) is a zero mean Gaussian process. We assume also that the phase θ is uniformly distributed on [0,2π]. The amplitude, A, of the oscillatory signal may be treated either as a constant or as a random number. It would appear appropriate to treat it as a random process in the context of our NEMS devices 10; however, we shall first look at the case of A being constant, since we will use those results in developing the analysis for the random amplitude case.

Single Observation

The first things we need in order to proceed are the probability density functions for the envelope-squared detector in the noise-only case and in the signal-plus-noise case. The probability density function of the noise-only process is found to be $$f_n(u) = \frac{1}{2\sigma_N^2} e^{-u/2\sigma_n^2}, u \geq 0 \qquad 1.14$$

where we have used $u=r^2$. FIG. 4 is a block diagram, which schematically shows the signal chain for this case. Device 10 has its output v(t) multiplied by the reference 34 by multiplier 35 with the product provided to low pass filter 36. The correlator output r(t) is provided to square law detector 38 to generate the signal, u(t). u(t) is provided as an input to a threshold detector 40 which passes the qualified signals to decision circuit 42 which implements the $H_0$-$H_1$ decision discussed above. The signal processing may be implemented in an analog or digital computer or processor pursuant to software, firmware or hardware control in a manner consistent with the teachings of the invention.

Figure 4:
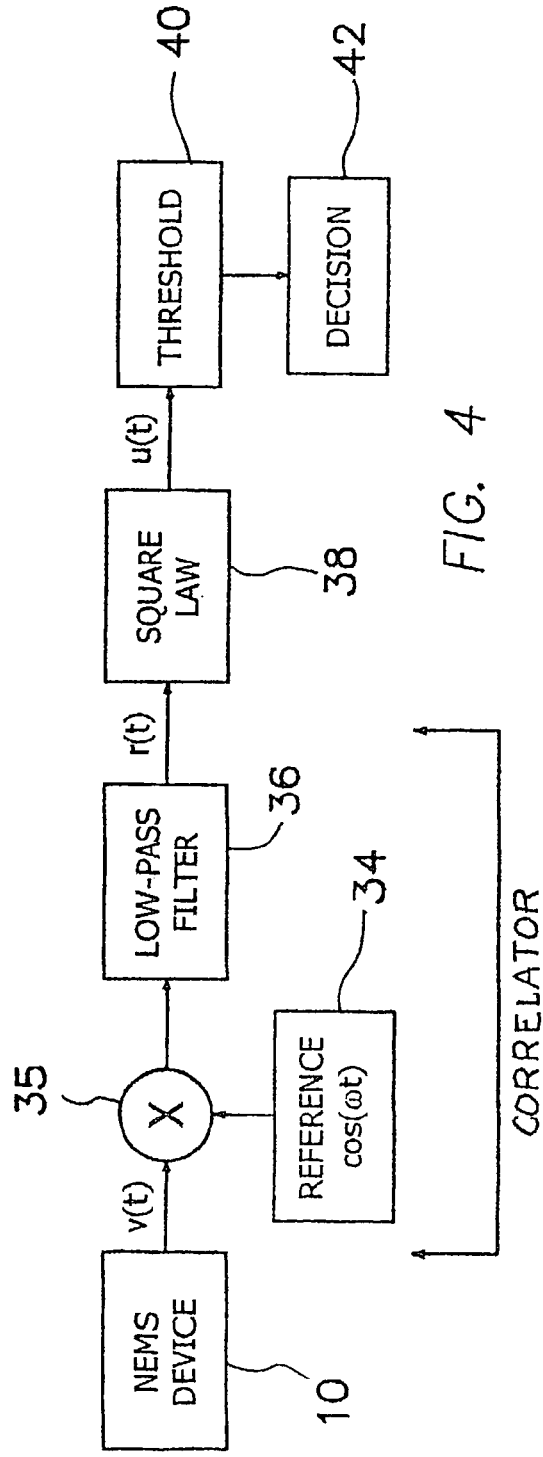
FIG. 4 is a block diagram of the signal chain provided in the invention for the case of a single observation.

The system shown in the FIG. 4 is close to optimum for low SNR signals for the case illustrated here. Note that the correlator output, r(t), can be treated as a narrowband signal, though in this case it appears as a low-pass filtered signal with bandwidth $B=\Omega_c$, where $\Omega_c$ is the effective cutoff frequency. The time-resolution of the overall system will be set by this cutoff frequency.

Next we develop an expression for the probability density function of the envelope-squared of the signal-plus-noise case by beginning with envelope detector, since this is the easiest route to our desired result. In this case we will write r(t) as $$r(t)=[A\cos\theta+x(t)]\cos(\omega_0 t)-[A\sin\theta+y(t)]\sin\omega_0 t$$

where x(t) and y(t) are zero-mean Gaussian signals representing the orthogonal components of the driving signal with equal variances of $\sigma^2_n$, and which are statistically independent. We may then write the envelope of r(t) as $$z(t)=\{[A\cos\theta+x(t)]^2+[A\sin\theta+y(t)]^2\}^{1/2} \qquad 1.16$$

Now, writing the quadrature components of z(t) corresponding to two orthogonal components as $$z_c(t)=A\cos\theta+x(t)$$

$$z_s(t)=A\sin\theta+y(t)$$

we then have $$z(t)=[z^2_c(t)+z^2_s(t)]^{1/2} \qquad 1.17$$

where again the $z_c$ and $z_s$ are zero-mean Gaussian independent random variables for any given θ, and furthermore we have for their mean and variance $$E\{z_c(t)\}=A\cos\theta,$$

$$E\{z_s(t)\}=A\sin\theta$$

$$V\{z_c(t)\}=V\{z_s(t)\}=\sigma^2_n$$

Here we use the usual notation, where E{•} denotes the expectation value, and V{•} is the variance.

From the above, we may now write the following conditional probability density function $$f_{z_c,z_s}(z_c, z_s[\theta]) = \frac{1}{2\pi\sigma_n^2}\exp[(z_c - A\cos\theta)^2 + (z_s - A\sin\theta)^2] \qquad 1.18$$

With the envelope given by $$z=[z_c^2+z_s^2]^{1/2} \; z\geq 0 \qquad 1.19$$

We define the new variable $$\phi = \tan^{-1}\left(\frac{z_s}{z_c}\right), 0 \leq \phi \leq 2\pi \qquad 1.20$$

with $$z_c=z\sin\phi$$

$$z_s=z\cos\phi \qquad 1.21$$

Using this transformation, we can now write the following conditional probability density function $$f_{z_c,z_s}(z_c, z_c[\theta]) = \frac{z}{2\pi\sigma_n^2}\exp\left[-\frac{1}{2\sigma_n^2}(z^2 + A^2 - 2Az\cos(\theta - \phi))\right] \qquad 1.22$$

Integrating this over the φ variable, we obtain $$f_z(z[\theta]) = \frac{z}{2\pi\sigma_n^2}\exp[-(z^2+A^2)/2\sigma_n^2]\int_0^{2\pi}\exp\left[\frac{Az}{\sigma_n^2}\cos(\theta-\phi)\right]d\phi \qquad 1.23$$

where the integral in this expression is given by $$2\pi I_0\left(\frac{Az}{\sigma_n^2}\right) \qquad 1.24$$

Now, since $f_z(z|\theta)$ is independent of $\theta$, we can immediately write the probability density function of the envelope as $$f_z(z) = \frac{z}{\sigma_n^2}\exp[-(z^2+A^2)/2\sigma_n^2]I_0\left(\frac{AZ}{\sigma_n^2}\right) \qquad 1.25$$

which is a Rician density function. Now, taking the envelope-squared to be $$u(t)=z^2(t)=[A\cos\theta+x(t)]^2+[A\sin\theta+y(t)]^2 \qquad 1.26$$

we can use a simple transformation of variables to find, from Eq (1.22), $$f_u\left(u|\theta\right) = \frac{1}{2\sigma_n^2}\exp[-(u+A^2)/2\sigma_n^2]I_0\left(\frac{A\sqrt{u}}{\sigma_n^2}\right) \qquad 1.27$$

Since $\theta$ is uniformly distributed on $0=\theta=2\pi$, integrating over the $\theta$ distribution gives immediately $$f_u(u) = \frac{1}{2\sigma_n^2}\exp[-(u+A^2)/2\sigma_n^2]I_0\left(\frac{A\sqrt{u}}{\sigma_n^2}\right) \qquad 1.28$$

We have to make one last modification to this expression in order to account for the presence of our narrowband filter. If $\rho$ is the ratio of NEMS device noise bandwidth to the bandwidth of our narrowband filter 36, then the effective noise variance is $$s^2_u=s^2_n/\rho \qquad 1.29$$

so that the correct probability density function in terms of the NEMS output variance is $$f_u(u) = \frac{\rho}{2\sigma_n^2}\exp[-(u+A^2)\rho/2\sigma_n^2]I_0\left(\frac{\rho A\sqrt{u}}{\sigma_n^2}\right) \qquad 1.30$$

This probability density function is in fact a special case of the non-central chi-squared distribution, and is the probability density function for our envelope-squared detector output, u(t). Thus, from Eqs (1.14) and (1.30) we can now compute the appropriate $P_{fa}$ and $P_d$ for our single-observation case. The results of these computations are shown below.

It is probably more realistic to consider the amplitude of our sinusoidal signal, A, to be a random variable, so we will provide a treatment for that case here. Taking the amplitude to be Gaussian with zero-mean and a variance $\sigma^2_a$ we will now write $$H_1: r(t)=a(t)\cos(\omega_0 t+\theta)+n(t)$$

Although we noted above that detection analysis is usually more easily carried out for the case of quadratic detection, in this particular case it is much easier to treat the envelope detector. So, given the Gaussian assumption for a(t) at the NEMS output 32, the probability density function of a(t) at the output of an envelope detector, will be the Rayleigh distribution $$f_a(a) = \frac{a}{\sigma_a^2}e^{-a^2/2\sigma_a^2} \qquad 1.32$$

For the envelope detector, the conditional probability density function of the signal-plus-noise output, from Eq (1.25), is given by $$f(q|a) = \frac{q}{\sigma_n^2}\exp\left[-\frac{1}{2\sigma_n^2}(q^2+a^2)\right]I_0\left(\frac{aq}{\sigma_n^2}\right) \qquad 1.33$$

Now, by averaging over the a(t) distribution $$f_q(q) = \int_0^\infty f_q(q|a)f_a(a)da \qquad 1.34$$

we can find the required probability density function. In anticipation of computing performance curves using an integral over the resulting distribution we define $s=\sigma^2_a/\sigma^2_n$. Furthermore, since we are putting everything in terms of ratios, we can arbitrarily take $\sigma^2_n$ to be unity for these calculations. This results in the following expression for probability density function of the envelope of the signal plus noise at the output of our envelope detector 38:

$$f_q(q) = qe^{-q^2/2}\int_0^\infty \frac{a}{s}\exp\left[\frac{-a^2(s+1)}{2s}\right]I_0(aq)da \qquad 1.35$$

Although this is a rather formidable looking integral, it has actually been tabulated, and after some appropriate substitutions for our particular case, we find our probability density function given by $$f_q(q) = \frac{1}{s+1}qe^{-q^2/2(s+1)}:H_1 \qquad 1.36$$

For the noise-only case, the envelope detector output probability density function is just $$f_q(q) = \frac{q}{\sigma_n^2}e^{-q^2/2\sigma_n^2}:H_0 \qquad 1.37$$

which is just the Rayleigh distribution again, this time for the thermal noise. We will use this density function in evaluating the false alarm probability, $P_{fa}$.

Multiple Observations

Figure 5:
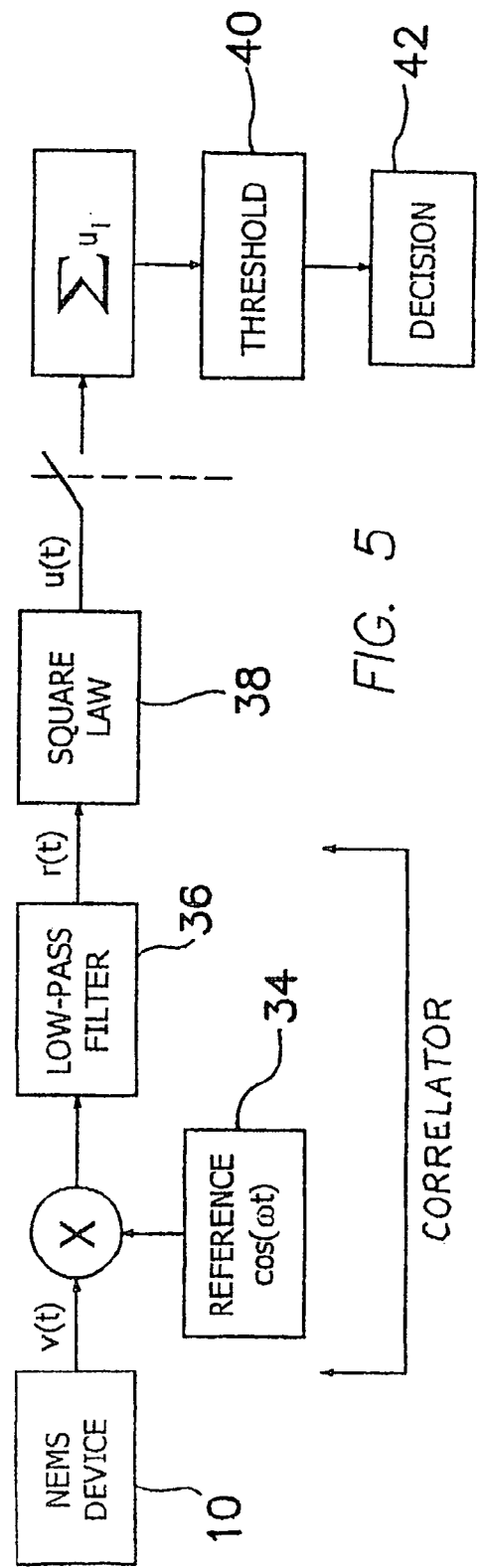
FIG. 5 is a block diagram of the signal chain provided in the invention for the case of multiple observations.

Now consider the expressions needed to evaluate the performance of a quadratic detector 38 followed by post-detection summation or equivalently discrete integration;

the signal chain is shown in the diagram of FIG. 5. FIG. 5 is identical to the arrangement of FIG. 4 with the exception that multiple observations or measurements generated in the output of square law detector 38 are sampled at step 94 and summed at step 46 whose output, q(t) is passed on to threshold detector 40 as before.

This case falls under the general noncentral Chi density and we now present several versions of this density that will be needed as we proceed. First, define the variable $$q' = \sum_{i=1}^{N}(A+x_i)^2$$

where the $x_i$ are, as usual here, taken to be identically distributed Gaussian random variables with zero mean and variance of $\sigma_n^2$. The form of the noncentral Chi-squared probability density function in this case is given by $$f_{q'}(q') = \frac{1}{2\sigma_n^2}\left(\frac{q'}{\alpha'}\right)^{(N-2)/4}\exp\left(-\frac{\alpha'+q'}{2\sigma_n^2}\right)I_{\frac{N}{2}-1}\left(\frac{\sqrt{\alpha'q'}}{\sigma_n^2}\right), q'>0 \qquad 1.39$$

The parameter, $\alpha'$, is called the noncentral parameter, and is given by $\alpha'=NA^2$. It is sometimes more useful to use a "normalized" variable, $q=q'/\sigma_n^2$, and then we have $$q = \sum_{i=1}^{N}\left(\frac{A}{\sigma_n}+\frac{x_i}{\sigma_n}\right), q>0 \qquad 1.40$$

with $$f_{q'}(q) = \frac{1}{2}\left(\frac{q}{\alpha}\right)^{(N-2)/4}\exp\left(-\frac{\alpha+q}{2}\right)I_{\frac{N}{2}-1}(\sqrt{\alpha q}) \qquad 1.41$$

where now we have $\alpha=NA^2/\sigma_n^2$.

Finally, we have the case where $$Q = \sum_{i=1}^{N}(A_i+x_i)^2 \qquad 1.42$$

which will be useful when we examine the situation where the amplitude of our oscillatory signal is itself a random variable. The noncentral Chi-squared probability density function for Q is $$f_Q(Q) = f_{q'}(q'), \alpha' = \sum_{i=1}^{N}A_i^2 \qquad 1.43$$

Now having the necessary density functions in hand, we first treat the case where the amplitude of our oscillatory signal, A, is assumed to be a constant, that depends only on the degree of coupling between the driven cantilever 28 and the responding cantilever 30. Again we take the output of the correlator to be represented by $$r(t)=n(t)H_0,$$

$$r(t)=A\cos(\omega_0 t+\theta)+n(t): H_1$$

From Eq (1.15), the output of the square-law detector 38, u(t), can be written as $$u(t)=[A\cos\theta+x(t)]^2+[A\sin\theta+y(t)]^2, \qquad 1.44$$

where, as before, x(t) and y(t) are zero-mean Gaussian variables with a variance of $\sigma_n^2$. This signal is now sampled at a rate determined by the bandwidth of the input filter 36, so that we will write $$q' = \sum_{i=1}^{N}(A\cos\theta+x_i)^2 + \sum_{i=1}^{N}(A\sin\theta+y_i)^2 \qquad 1.45$$

where the maximum number of samples, N, will be determined by the sampling rate and the observation time, T. Note also that the maximum observation time will be limited by $\tau$, which is the first zero in the autocorrelation function describing the transfer function of the correlator, and so it is related to the bandwidth of the filter 36. Inserting the explicit expression for the $u_i(t)$, and suppressing the time dependence, we have $$q' = \sum_{i=1}^{N}(A\cos\theta+x_i)^2 + \sum_{i=1}^{N}(A\sin\theta+y_i)^2 \qquad (1.46)$$

which is just the noncentral Chi-squared probability density function of Eq (1.29), with 2N degrees of freedom, and noncentral parameters given by $$\alpha_1=NA^2\cos^2\theta$$

$$\alpha_2=NA^2\sin^2\theta \qquad 1.47$$

where we have dropped the prime notation.

As we saw earlier, it is convenient to use the "normalized" variable $q=q'/s2n$ so that Eq (1.36) becomes $$q = \sum_{i=1}^{N}\left(\frac{A\cos\theta}{\sigma_n}+\frac{A\sin\theta}{\sigma_n}\right)^2 \qquad 1.48$$

The noncentral parameters are now $$\alpha_1=NA^2\cos^2\theta/\sigma_n^2$$

$$\alpha_2=NA^2\sin^2\theta/\sigma_n^2 \qquad 1.49$$

We may now write the probability density function of our test statistic, q, as $$f_q(q) = \frac{1}{2}\left(\frac{q}{\alpha}\right)^{(N-2)/4}\exp\left(-\frac{\alpha+q}{2}\right)I_{\frac{N}{2}-1}\sqrt{\alpha'q'} \qquad 1.50$$

with $\alpha=NA^2/\sigma_n^2$. Interestingly, the noncentral parameter divided by the number of degrees of freedom, $$\frac{\alpha}{2N} = \frac{A^2}{2\sigma_n^2} \qquad 1.51$$

is just one-half the (power) SNR at the input to the square-law device 38. Finally, the noise-only probability density function for this case is given by a Gamma distribution:

$$f_q(q) = \frac{q^{N-1}}{2^N(\sigma_n^2)^N \Gamma(N)} e^{-q/2\sigma_n^2} \qquad 1.52$$

We can now use Eq (1.51) and (1.53) to compute the performance curves for this case, and the results are shown below.

In what follows, all of the performance plots show power SNR; the equivalent voltage SNR is just the square root of this number. Also, insofar as possible, we have tried to relate the SNR to the physical quantity that is affected by the presence or absence of target biomolecules, $\gamma_e$. Dropping the "e" subscript for convenience, we can write $\Delta\gamma=|\gamma_b-\gamma_u|$. We can relate $\Delta\gamma$ to the NEMS device output variance by recalling from Eq (1.4) that $$\langle x^2(t) \rangle = \frac{4k_B T \gamma}{\kappa^2} \qquad 1.53$$

and so $$\langle v^2(t) \rangle = K\langle x^2(t) \rangle = K\frac{4k_B T \gamma}{\kappa^2} \qquad 1.54$$

where we have defined K=[GI]2 using Eq (1.5). And so we have for the bound and unbound cases $$\Delta(\sigma^2) = |\sigma_b^2 - \sigma_u^2| = K\frac{4k_B T \Delta(\gamma)}{\kappa^2} \qquad 1.55$$

In fact, we can express the output (power) SNR of device 10 as $$SNR_0 = \sigma_b^2/\sigma_n^2 = \gamma_b/\gamma_u \qquad 1.56$$

It should be noted that this applies directly only to the passive configuration. Interpretation of "signal" in the active cases will depend on the details of the particular configuration used, e.g., the configuration of FIG. 2b, detects the presence of target molecules 26 when the cantilever "uncouples" from the substrate 34. This means that when no target molecules 22 are present, the responding cantilever 30 is constrained so that it cannot be effectively stimulated to oscillate by the reference (driven) cantilever 28. The presence of target molecules 22 will cause this constraint to be removed, by the mechanism of competitive binding, and the responder 30 can then "couple" to the driven cantilever 28 and produce an oscillating component in its output. The performance characteristics for this specific configuration are presented below. In the future, we will develop performance characteristics for other active configurations that may seem promising.

Figure 6:
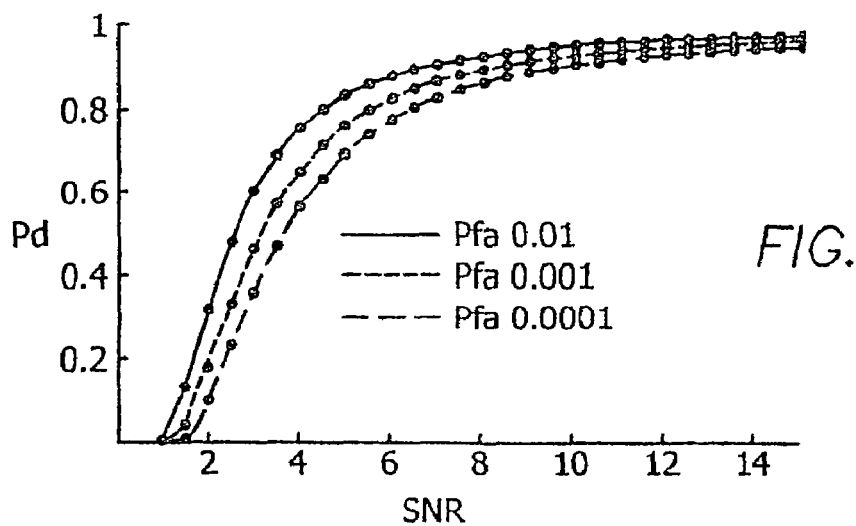
FIG. 6 is a graph of the detection performance for a device operated in the passive configuration.

We begin by presenting the results for the one-port passive embodiment, which we analyzed above on the basis of a signal chain consisting of a narrowband filter 36 followed by an envelope detector 38. FIG. 6 is a graph which shows the detection performance as a function of the SNR for three values of $P_{fa}$, which SNR is the simple power-valued SNR. Thus, for example, a displayed SNR of 10, corresponds to a voltage. SNR of about 3.2, and yields a probability of detection of about 90 percent at a $P_{fa}$ of 0.0001.

Figure 7:
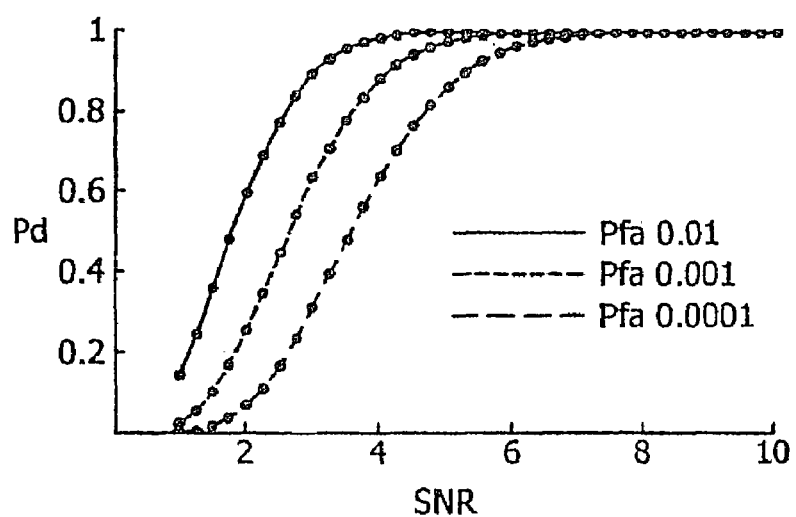
FIG. 7 is a graph of the detection performance for a device operated in the active configuration for a single observation.

As is to be expected, the single observation active case, where we assumed the "signal" amplitude, A, was constant, and this shows much better performance. This case is shown in FIG. 7, where we chose an extremely modest bandwidth ratio of only 5. The SNR for this case is defined by $SNR=A^2/\sigma_n^2$. Note that there is an as yet unknown parameter implicit in the signal amplitude, which is the average value of the fluid "coupling constant" between the driven cantilever 28 and the responding cantilever 30.

Figure 8:
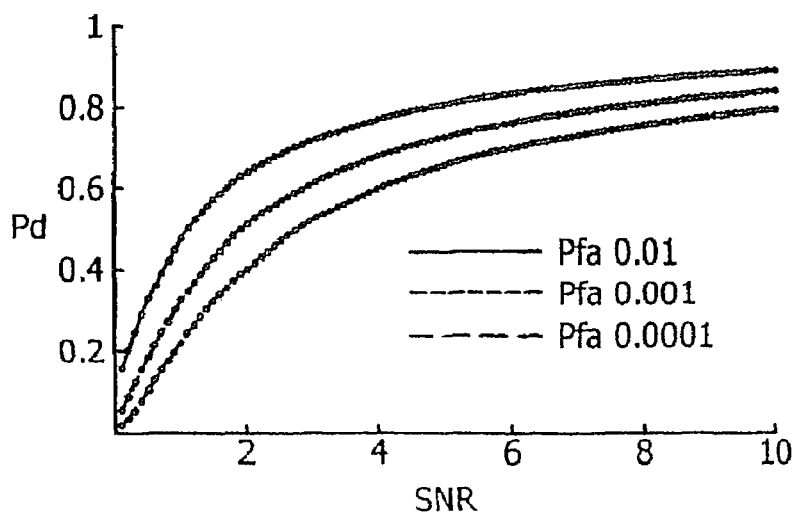
FIG. 8 is a graph of the detection performance for the case of a fluctuating signal amplitude.

We also treated a variation on the above case where we assumed that the amplitude of our oscillatory signal was itself a random variable, i.e., that it fluctuates in a nondeterministic way. The results of that analysis are presented in FIG. 8, where we again calculate the expected performance $P_d$ for three values of $P_{fa}$; and have again chosen a bandwidth ratio of five. Note also, that in this case we define the SNR as the ratio of the mean signal power to the noise power. Note that the performance for this case is poorer than the previous case, since there we assumed the signal amplitude to be a constant.

At this stage of our investigations, we cannot yet provide a more explicit relationship between the SNR performance and the physical device characteristics, since we do not have a method for estimating the degree of fluid "coupling" to be expected between the driver cantilever 28 and the responder 30.

Figure 9:
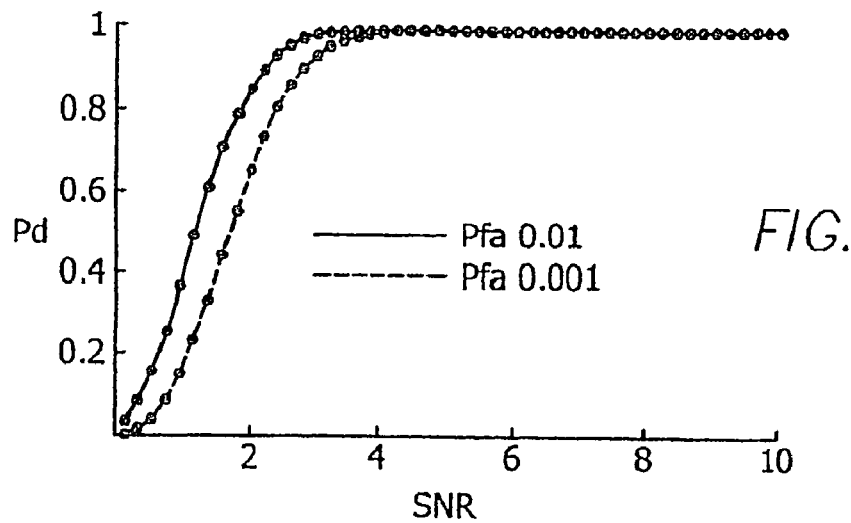
FIG. 9 is a graph of the detection performance for sampling/summation.

Finally, we present results for the last case considered, that of discrete sampling followed by summation of N samples. FIG. 9 shows these results for N=20, and a bandwidth ratio of five. Recall that in this case we treated the oscillatory signal amplitude as being a constant, A, and thus we have $SNR=A^2/\sigma_n^2$ for this case. Note that this case is simply a digital signal integrator, that integrates over an interval, T, that is determined by the bandwidth of the signal chain.

We have analyzed several NEMS device embodiments with respect to their expected signal detection performance. We should emphasize that the embodiments used for purposes of these analyses are not necessarily optimum from a fabrication standpoint. We can state that our force sensitivity estimates are eminently achievable, and that we can build practical devices that can detect the presence of extremely dilute solutions of biomolecules at the stochastic limit.

Undriven Single Cantilever using a Chopped Signal

Figure 12:
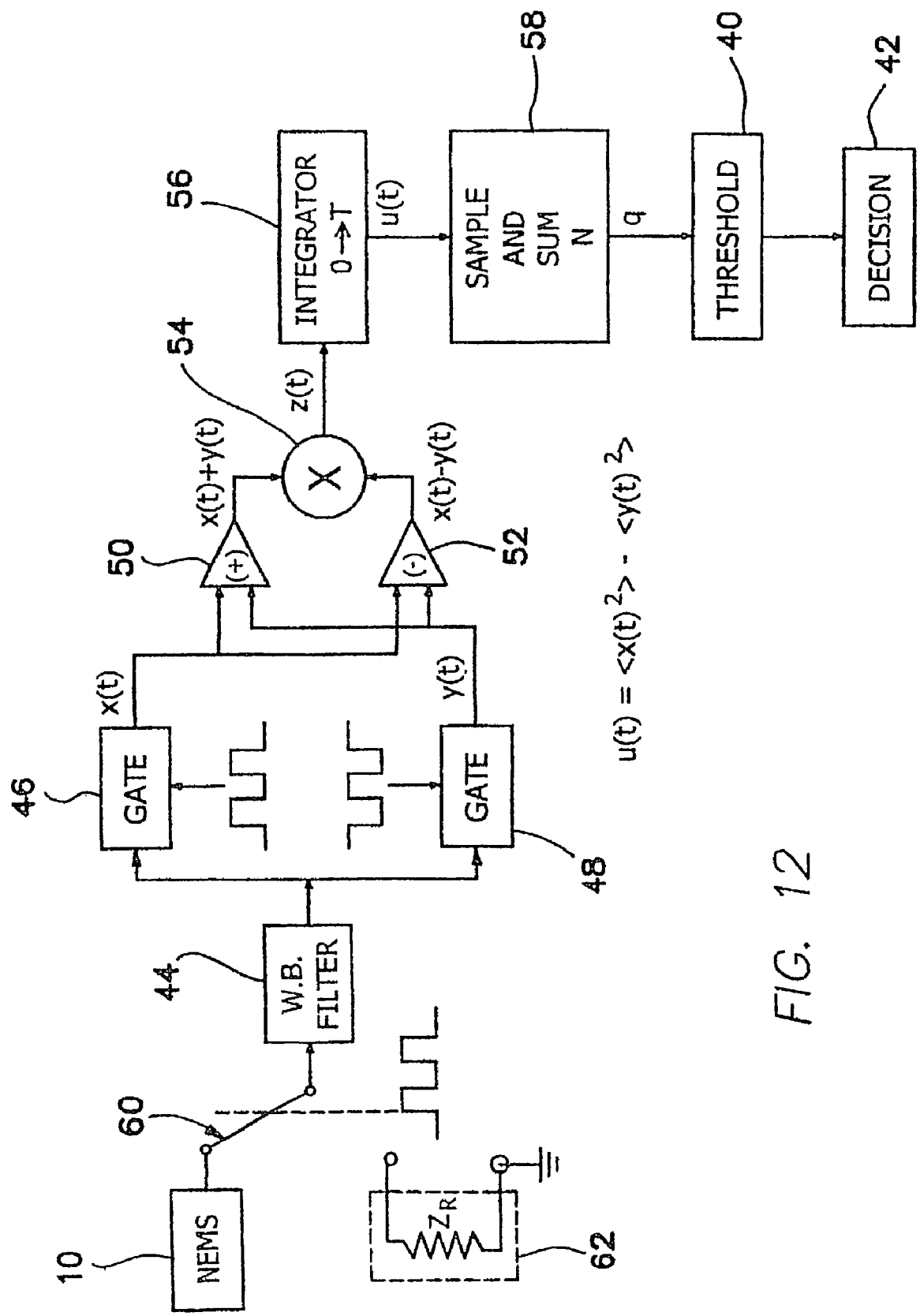
FIG. 12 is a schematic block diagram of a detector corresponding to the graph of FIG. 10.

FIG. 12 is a schematic showing the signal chain for an undriven single cantilever 12 as shown in FIG. 1 using a chopped signal. The input signal is chopped by a switch 60 between device 10 and a reference input impedance, $Z_R$. The chopped signal is filtered by a wide bandwidth filter 44 and then divided by quadrature gate 46 for the x(t) component and gate 48 for the y(t) component which are 180 degrees out of phase with each other. The output of gates 46 and 48 are each provided to an adder 50 and a subtractor 52. The sum and difference of the quadrature signals are multiplied by multiplier 54 to provide the signal z(t). The product z(t) is integrated over the chopped pulse width T by integrator 56 to generate the signal, u(t). The integrated signal, u(t), is sampled and summed for N observations or measurements by circuit 58 to provide the signal, q(t). Threshold circuit 40 as before tests q to determine if it meets the predetermined thresholds (e.g. acceptable $P_{fa}$) and then a decision is made by circuit 42 as before according to the algorithm, eqn. 1.36, 1.37. While the elements of FIGS. 4, 5 and 12 have been described as hardware or software controlled circuit elements, the diagrams can also be interpreted as steps in a method of signal processing.

Figure 10:
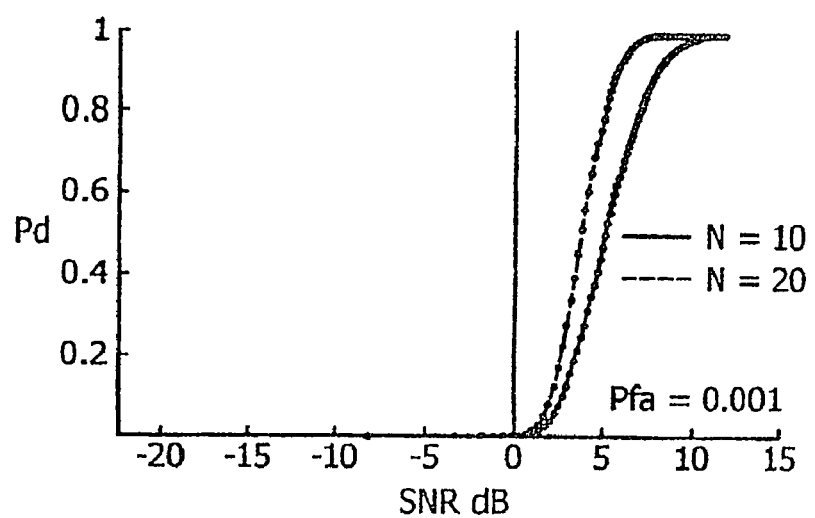
FIG. 10 is a graph of detection performance for a chopped signal detection method.
Figure 11:
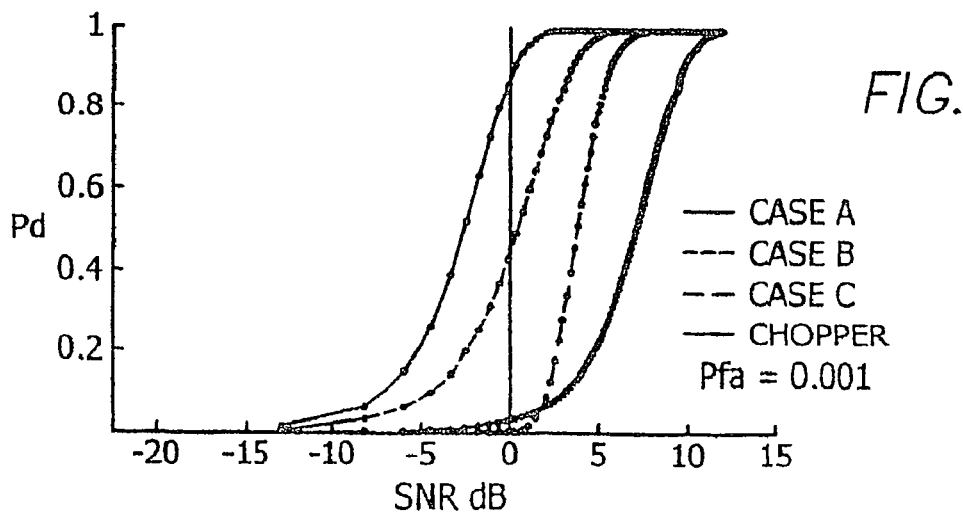
FIG. 11 is a graph of detection performance for a comparison of various performance configurations.

Shown in FIGS. 10 and 11 are two performance curves using a modification to the chopped noise detector embodiment described above in FIG. 12. It has been modified to incorporate multiple-sample summation, and the two plots are for summation over 10 and 20 samples. Note that this uses a single, undriven cantilever 12 as the NEMS device 10. Another interesting aspect of this approach is that we are not nearly as limited by bandwidth constraints in applying this to the stochastic chemistry application. In fact, this approach works at bandwidths up to about 500 kHz or greater.

Figure 2C:
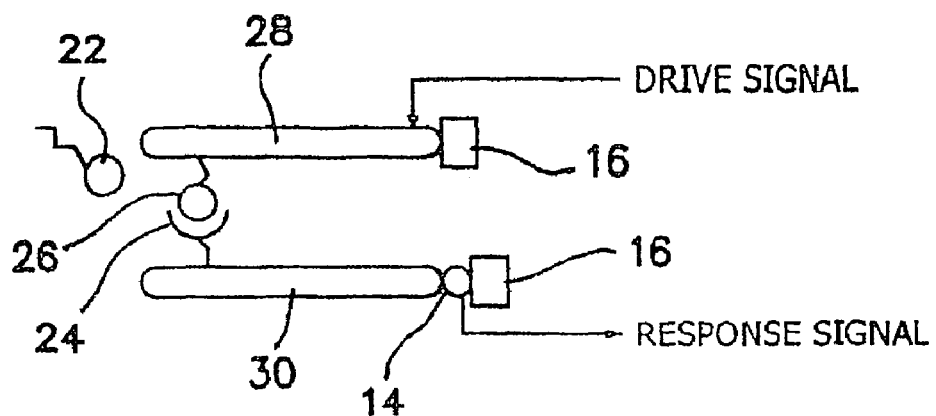

FIG. 11 shows a comparison of the performance of the detector for a single undriven cantilever 12 with the previous results obtained for the driven cantilever embodiment of FIGS. 2a-2c. It can be seen that it compares favorably with the driven case where the oscillating signal amplitude of the driving signal is subject to fluctuations. The performance curve for $P_d$ for the undriven cantilever 12 lies between Case B and Case C for the driven cantilever 28, and represents summation over 20 data samples. Case A is the situation where neither amplitude nor phase are random, case B is the situation where amplitude is a random variable, and case C is the situation where phase is a random variable.

Cantilevers and Reaction Probabilities

In addition to calculating the number of "hits" per second by ligand molecules on a functionalized area of a cantilever 12, 28 or 30, we ultimately need to derive an expression for the expected number of ligand-receptor binding reactions per second, i. e., the reaction probability per unit time. The traditional approach simply computes the pair collision probability (per unit time) from the kinetics of hard spheres of radii, $r_1$ and $r_2$, having a "collision" radius of $r_1+r_2$. This is converted to a reaction probability by multiplying by an Arrhenius factor given by $\text{Exp}[-U_a/k_BT]$, where $U_a$ is the reaction activation energy. For our situation, where the receptors 24 are "fixed" in a two-dimensional space, and considered uniformly distributed in the functionalized area of dA, we can express the effective pair collision probability by using the expression for the flux $\Gamma$ of molecules through a plane area, dA, $$\Gamma_I = \frac{1}{4} \frac{X_I}{V} \langle v_I \rangle dA \qquad 2.1$$

where V is the chamber volume containing the ligands 22, $v_I$ is the speed of ligand, I, the subscript I refers to ligand 22, and $X_I$ denotes the number of molecules of specie I, and the mean speed is given by $$\langle V_I \rangle = \sqrt{\frac{8RT}{\pi M_I}}. \qquad 2.2$$

Here, R is the usual "gas constant", and $M_I$ is the (molar) mass of the ligand, I.

Now, the relative speed of the two reactants is simply the mean speed given by (Eqn 2.2), and Eqn (2.1) gives the number of ligand molecules 22 incident on our "array" of receptors 24, so we can write the total effective reaction probability (per unit time) as $$P(r) = \frac{X_I X_T}{4V_0} \pi R_{12}^2 \sqrt{\frac{8RT}{\pi M_I}} \ e^{-U_a/RT} \qquad 2.3$$

where $R_{12}$ is the collision radius, and $V_0$ is the NEMS "chamber" volume. Notice that our result is independent of the actual area of the functionalized region, and depends on the number density of ligand molecules 22 and total number of receptors 24.

We have done a calculation of the expected reaction probability using this expression for the following assumptions: $50\times50\times50$ $\mu^3$ volume, 1000 ligand molecules 22, 100 receptor molecules 24, a collision radius of 50 nm, a ligand mass of 20 kDa, and an activation energy of 10 kJmole$^{-1}$. These values yield a reaction probability (rate) of approximately 1825 s$^{-1}$. This certainly is a very favorable result; however, note that an activation energy of only 10 kJmole$^{-1}$ is a very small value. Activation energies typically are in the 50-100 kJmole$^{-1}$ range, and since it appears in the exponent of the Arrhenius factor, it makes a very large difference in the reaction probability. For the case of massive biomolecules the collision probability term will in general be much smaller than what one is used to in dealing with reactions involving small molecules because the relative speeds are so much smaller for these large molecules 22, and you do not really pick up the difference in the larger collision radii. As an example, for inorganic bimolecular reactions in three dimensional liquid systems, the collision probability term is usually of the order $10^{11}$, (excluding the $X_I X_r$ factor) and the activation energies are greater than 100 kJmole$^{-1}$.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must/be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method of sensing a signal from an oscillating bioNEMs transducer comprising:
   generating an output signal from the oscillation of the transducer;
   mixing the output signal with a reference signal;
   filtering the mixed output signal to generate a correlator output, r(t);
   detecting the correlator output to generate a signal u(t);
   determining whether the signal u(t) satisfies a predetermined threshold; and
   deciding whether the signal u(t) represents a predetermined type of interaction between a free ligand in a fluid and a receptor attached to the transducer.

2. The method of claim 1 where determining whether the signal u(t) satisfies a predetermined threshold comprises applying the Neyman-Pearson criterion based on a predetermined probability of false detection, $P_{fa}$.

3. The method of claim 1 where determining whether the signal u(t) satisfies a predetermined threshold comprises determining whether a likelihood ratio of probability density functions of bound and unbound configurations of the ligand and receptor has a predetermined value.

4. The method of claim 1 where deciding whether the signal u(t) represents an predetermined type of interaction between a free ligand in a fluid and a receptor attached to the transducer comprises deciding based on u(t) whether the ligand has bound to the receptor.

5. The method of claim 1 where deciding whether the signal u(t) represents an predetermined type of interaction between a free ligand in a fluid and a receptor attached to the transducer comprises deciding based on u(t) whether a bound ligand has been released from the receptor by competitive binding with the free ligand.

6. The method of claim 1 where detecting the correlator output to generate a signal u(t) comprises squaring the signal, r(t).

7. The method of claim 1 where detecting the correlator output to generate a signal u(t) comprises detecting the envelope of the signal, r(t).

8. The method of claim 1 further comprising sampling a plurality of measurements of the signal, u(t) and summing the sample signals to generate a signal, q(t), which is then tested for qualification relative to a threshold and from which qualified signals a decision is made as to the interaction which as occurred between the free ligand and receptor.

9. The method of claim 1 further comprising:
   providing the NEMS transducer with an attached bioreceptor;
   exposing the biofunctionalized transducer to a free ligand in fluid;
   interacting the free ligand with the bioreceptor to provide an interaction therebetween; and
   oscillating the transducer to detect the existence of the interaction between the bioreceptor and free ligand.

10. The method of claim 1 where generating a output signal from the oscillation of the transducer comprises oscillating a piezoresistive transducer by means of thermal fluctuations.

11. The method of claim 1 where generating a output signal from the oscillation of the transducer comprises oscillating a piezoresistive transducer by means of a driving signal.

12. The method of claim 1 where generating a output signal from the oscillation of the transducer comprises oscillating a piezoresistive transducer by means of oscillating a coupled second transducer.

13. The method of claim 12 where oscillating a piezoresistive transducer by means of oscillating a coupled second transducer comprises coupling the piezoresistive transducer with the second transducer by fluid coupling therebetween.

14. The method of claim 12 where oscillating a piezoresistive transducer by means of oscillating a coupled second transducer comprises coupling the piezoresistive transducer with the second transducer by ligand coupling therebetween.

15. The method of claim 1 further comprising providing a substrate and ligand coupling the transducer to the substrate.

16. A method of sensing a signal from an oscillating bioNEMs transducer comprising:
   generating an output signal from the oscillation of the transducer;
   chopping the output signal in time;
   filtering the chopped output signal to generate a correlator output, r(t);
   generating summed and differenced quadrature components of the filtered chopped signal;
   multiplying the summed and differenced quadrature components to generate a signal, z(t);
   integrating z(t) over a sample period, T, to generate a signal, u(t);
   summing multiple measurements of z(t) over N sample periods to generate a signal, q(t);
   determining whether the signal u(t) satisfies a predetermined threshold; and
   deciding whether the signal u(t) represents an predetermined type of interaction between a free ligand in a fluid and a receptor attached to the transducer.

17. The method of claim 16 where determining whether the signal u(t) satisfies a predetermined threshold comprises applying the Neyman-Pearson criterion based on a predetermined probability of false detection, $P_{fa}$.

18. The method of claim 16 where determining whether the signal u(t) satisfies a predetermined threshold comprises determining whether a likelihood ratio of probability density functions of bound and unbound configurations of the ligand and receptor has a predetermined value.

19. The method of claim 16 where deciding whether the signal u(t) represents an predetermined type of interaction between a free ligand in a fluid and a receptor attached to the transducer comprises deciding based on u(t) whether the ligand has bound to the receptor.

20. The method of claim 16 where deciding whether the signal u(t) represents an predetermined type of interaction between a free ligand in a fluid and a receptor attached to the transducer comprises deciding based on u(t) whether a bound ligand has been released from the receptor by competitive binding with the free ligand.

21. An apparatus for sensing an output signal from an oscillating bioNEMs transducer comprising:
mixing means coupled to the transducer for mixing the output signal with a reference signal;
filtering means coupled to the mixing means for filtering the mixed output signal to generate a correlator output, r(t);
detector means coupled to the filtering means for detecting the correlator output to generate a signal u(t);
threshold means coupled to the detector means for determining whether the signal u(t) satisfies a predetermined threshold; and
decision means coupled to the threshold means for deciding whether the signal u(t) represents a predetermined type of interaction between a free ligand in a fluid and a receptor attached to the transducer.

22. The apparatus of claim 21 where the threshold means comprises means for applying the Neyman-Pearson criterion, based on a predetermined probability of false detection, $P_{fa}$.

23. The apparatus of claim 21 where the threshold means for determining whether a likelihood ratio of probability density functions of bound and unbound configurations of the ligand and receptor has a predetermined value.

24. The apparatus of claim 21 where decision means comprises means for deciding based on u(t) whether the ligand has bound to the receptor.

25. The apparatus of claim 21 where the decision means comprises means for deciding based on u(t) whether a bound ligand has been released from the receptor by competitive binding with the free ligand.

26. The apparatus of claim 21 where the detector means comprises means for squaring the signal, r(t).

27. The apparatus of claim 21 where the detector means comprises means for detecting the envelope of the signal, r(t).

28. The apparatus of claim 21 further comprising sampling means coupled to the detector means for sampling a plurality of measurements of the signal, u(t) and integration means for summing the sample signals to generate a signal, q(t), which is then tested for qualification relative to a threshold and from which qualified signals a decision is made as to the interaction which as occurred between the free ligand and receptor.

29. The apparatus of claim 21 where the NEMS transducer has an attached bioreceptor which is biofunctionalized to a free ligand in fluid, such that interaction of the free ligand with the bioreceptor is detected by an effect on the oscillation of the transducer.

30. The apparatus of claim 21 further comprising means for generating a output signal from the oscillation of the transducer which means comprises a piezoresistive transducer oscillated by means of thermal fluctuations.

31. The apparatus of claim 21 further comprising means for generating a output signal from the oscillation of the transducer which means comprises a piezoresistive transducer oscillated by means of an external driving signal.

32. The apparatus of claim 21 further comprising means for generating a output signal from the oscillation of the transducer which means comprises a piezoresistive transducer oscillated by means of an oscillating coupled second transducer.

33. The apparatus of claim 32 where the piezoresistive transducer is oscillated by means of fluid coupling with the second transducer.

34. The apparatus of claim 32 where the piezoresistive transducer is oscillated by means of ligand coupling with the second transducer.

35. The apparatus of claim 21 further comprising a substrate which is ligand coupled to the transducer.

36. An apparatus for sensing an output signal from an oscillating bioNEMs transducer comprising:
chopper means coupled to the transducer for chopping the output signal in time;
filtering means coupled to the chopper means for filtering the chopped output signal to generate a correlator output, r(t);
quadrature means coupled to the filtering means for generating summed and differenced quadrature components of the filtered chopped signal;
mixing means coupled to the quadrature means for multiplying the summed and differenced quadrature components to generate a signal, z(t);
integration means coupled to the mixing means for integrating z(t) over a sample period, T, to generate a signal, u(t);
summing means coupled to the integration means for summing multiple measurements of z(t) over N sample periods to generate a signal, q(t);
threshold means coupled to the summing means for determining whether the signal u(t) satisfies a predetermined threshold; and
decision means coupled to the threshold means for deciding whether the signal u(t) represents an predetermined type of interaction between a free ligand in a fluid and a receptor attached to the transducer.

37. The apparatus of claim 36 where the threshold means comprises means for applying the Neyman-Pearson criterion based on a predetermined probability of false detection, $P_{fa}$.

38. The apparatus of claim 36 where the threshold means comprises means for determining whether a likelihood ratio of probability density functions of bound and unbound configurations of the ligand and receptor has a predetermined value.

39. The apparatus of claim 36 where the decision means comprises means for deciding based on u(t) whether the ligand has bound to the receptor.

40. The apparatus of claim 36 where the decision means comprises means for deciding based on u(t) whether a bound ligand has been released from the receptor by competitive binding with the free ligand.

* * * * *